US005600031A

United States Patent [19]
Roussel

[11] Patent Number: 5,600,031
[45] Date of Patent: Feb. 4, 1997

[54] PROCESS FOR PREFORMING COBALTOUS SALTS USING SHELL-TYPE PREFORMER CATALYSTS

[75] Inventor: Patricia B. Roussel, Baton Rouge, La.

[73] Assignee: Exxon Chemical Patents, Inc., Wilmington, Del.

[21] Appl. No.: 516,537

[22] Filed: Aug. 18, 1995

[51] Int. Cl.$^6$ ............................ C07C 27/20; C07C 31/125
[52] U.S. Cl. ........................... 568/882; 502/28; 568/451; 568/883
[58] Field of Search ................................ 568/882, 883, 568/451

[56] References Cited

U.S. PATENT DOCUMENTS

| | | | |
|---|---|---|---|
| 5,196,617 | 3/1993 | Kovenklioglu et al. | 570/204 |
| 5,321,168 | 6/1994 | Roussel et al. | |
| 5,406,006 | 4/1995 | Hill et al. | 568/451 |
| 5,434,318 | 7/1995 | Hill et al. | 568/882 |
| 5,457,240 | 10/1995 | Beadle et al. | 568/882 |

FOREIGN PATENT DOCUMENTS

| | | |
|---|---|---|
| 565952 | 10/1993 | European Pat. Off. |
| WO93/18856 | 9/1993 | WIPO. |

OTHER PUBLICATIONS

Usami et al., "Synthetic Studies of Co Carbonyl by Noble Metal Catalysts. I", Bulletin of the Chemical Society of Japan, vol. 42, pp. 2961–2965 (1969).

Usami et al., "Synthetic Studies of Co Carbonyl by Noble Metal Catalysts. II", Bulletin of the Chemical Society of Japan, vol. 42, 2966–2970 (1969).

"Platinum Metal Review", Johnson Matthey, vol. 38, No. 2, pp. 125–132 (Apr. 1994).

Primary Examiner—Joseph E. Evans
Attorney, Agent, or Firm—Richard D. Jordan; John F. Hunt

[57] ABSTRACT

A process for preparing oxo alcohols and aldehydes by the cobalt catalyzed hydroformylation of $C_2$ to $C_{17}$ linear or branched monoolefins with subsequent hydrogenation of the hydroformylation product, in which oxo process aqueous solutions of cobalt salts are converted to active hydrido cobalt carbonyl species in a preformer reactor under preforming reaction conditions, the improvement characterized by the preformer reactor containing a shell-type, metal on substrate, preformer catalyst.

12 Claims, 2 Drawing Sheets

PROCESS FOR PREFORMING COBALTOUS SALTS USING SHELL-TYPE PREFORMER CATALYSTS

The present invention relates to the oxo process for preparing oxo alcohols by the hydroformylation of olefins. More particularly, this invention relates to the use of a shell-type, metal on substrate, catalyst which is capable of preforming cobaltous salts, e.g., cobalt formate, in aqueous solutions to hydrido cobalt tetracarbonyl.

BACKGROUND OF THE INVENTION

The oxo process is the commercial application of the hydroformylation reaction for making higher alcohols and aldehydes from olefins. In the cobalt oxo process, an olefin reacts with carbon monoxide and hydrogen (i.e., syn gas) at elevated temperatures in the presence of a cobalt carbonyl catalyst to produce a hydroformylation reaction product which is subsequently decobalted or demetalled to produce a crude product mixture of aldehydes, alcohols, acetals, formates, unreacted olefins and secondary products. Subsequent hydrogenation steps provide the desired finished alcohol products commonly referred to as oxo alcohols (i.e., alcohols produced by an oxonation reaction).

One aspect of the overall cobalt oxo process involves the preparation of the active cobalt catalyst species which is hydrido cobalt tetracarbonyl ($HCo(CO)_4$). Commercial oxo processes employ a preforming step in which this active cobalt catalyst species is prepared using a noble metal preforming catalyst which is contacted with a cobalt salt, e.g., cobalt formate, to provide the desired $HCo(CO)_4$ species.

This preforming step is disclosed, for example, in U.S. Pat. No. 4,404,119, which issued Sep. 13, 1983, to Lagace et al. and in U.S. Pat. No. 4,255,279, which issued Mar. 10, 1981, to Spohn et al., and U.S. Pat. No. 5,237,105, which issued Aug. 17, 1993, to Summedin, all of which are incorporated herein by reference.

Particularly preferred preformer catalysts are set forth in co-pending U.S. patent application, Ser. No. 08/217,298 (Hill, Jr. et al.), which was filed on Mar. 22, 1994, now U.S. Pat. No. 5,434,318. These conventional preformer catalysts comprise Group IB and VIII metals such as palladium, platinum or gold. Such catalysts may be supported or unsupported using supports such as silica, alumina, zeolites or activated carbon and other carbonaceous support material. One particularly desirable preformer catalyst is 2 wt. % palladium supported on activated carbon.

The present inventor has discovered that the use of a shell-type, metal on substrate, catalyst wherein the metal is placed on the exterior surface of the substrate as opposed to being uniformly impregnated throughout the entire substrate as are the catalyst disclosed in co-pending U.S. patent application, Ser. No. 08/217,298 (Hill, Jr. et al.), allows for improved conversion of the cobaltous salt to hydrido cobalt tetracarbonyl in the preformer reactor.

The increased process efficiency obtained by utilizing the shell-type, metal on substrate, catalyst translates into increased processing capacity for a given commercial scale reactor. Reactor vessels can be reduced in size in direct proportion to the rate constant improvement allowing significant reduction in initial capital investment for the preformer reactor.

Still another advantage of the present invention is reduced catalyst cost while maintaining processing capacity. That is, a smaller amount of the shell-type catalyst of the present invention is required to convert a cobalt salt to the desired $HCo(CO)_4$ compared to the amount required by conventional preformer catalysts to attain similar conversion levels.

The present invention also provides many additional advantages which shall become apparent as described below.

SUMMARY OF THE INVENTION

A process for preparing oxo alcohols and aldehydes by the cobalt catalyzed hydroformylation of $C_2$ to $C_{17}$ linear or branched monoolefins with subsequent hydrogenation of the hydroformylation product, in which oxo process aqueous solutions of cobalt salts are converted to active hydrido cobalt carbonyl species in a preformer reactor under preforming reaction conditions, the preformer reactor containing a shell-type, metal on substrate, preformer catalyst.

The metal is preferably selected from a metal of Group IB or Group VIII of the Periodic Table, e.g., palladium. The substrate is preferably selected from the group consisting of: activated carbon, ion exchange resins, silica, alumina and zeolites, preferably activated carbon.

The oxo process aqueous solutions of cobalt salts are preferably converted to active hydrido cobalt carbonyl species in a preformer reactor in the presence of the preformer catalyst, hydrogen and carbon monoxide at a pressure in the range between about 20.8 to 27.7 MPa and a temperature in the range between about 120° to 150° C.

The preformer catalyst is a shell-type, metal on substrate, catalyst which comprises 0.3 to 5% by weight metal on the substrate. This shell-type, metal on substrate, catalyst is preferably formed by the following steps: impregnating the substrate with an aqueous metal salt solution; precipitating the metal; and reducing the metal. The impregnation procedure is carried out such that the metal contained within the aqueous metal salt solution preferably impregnates the surface of the substrate to a depth between about 0.10 to 0.15 mm.

Other and further objects, advantages and features of the present invention will be understood by reference to the following specification in conjunction with the annexed drawings, wherein like parts have been given like numbers.

DESCRIPTION OF THE PREFERRED EMBODIMENTS

Figure 1:
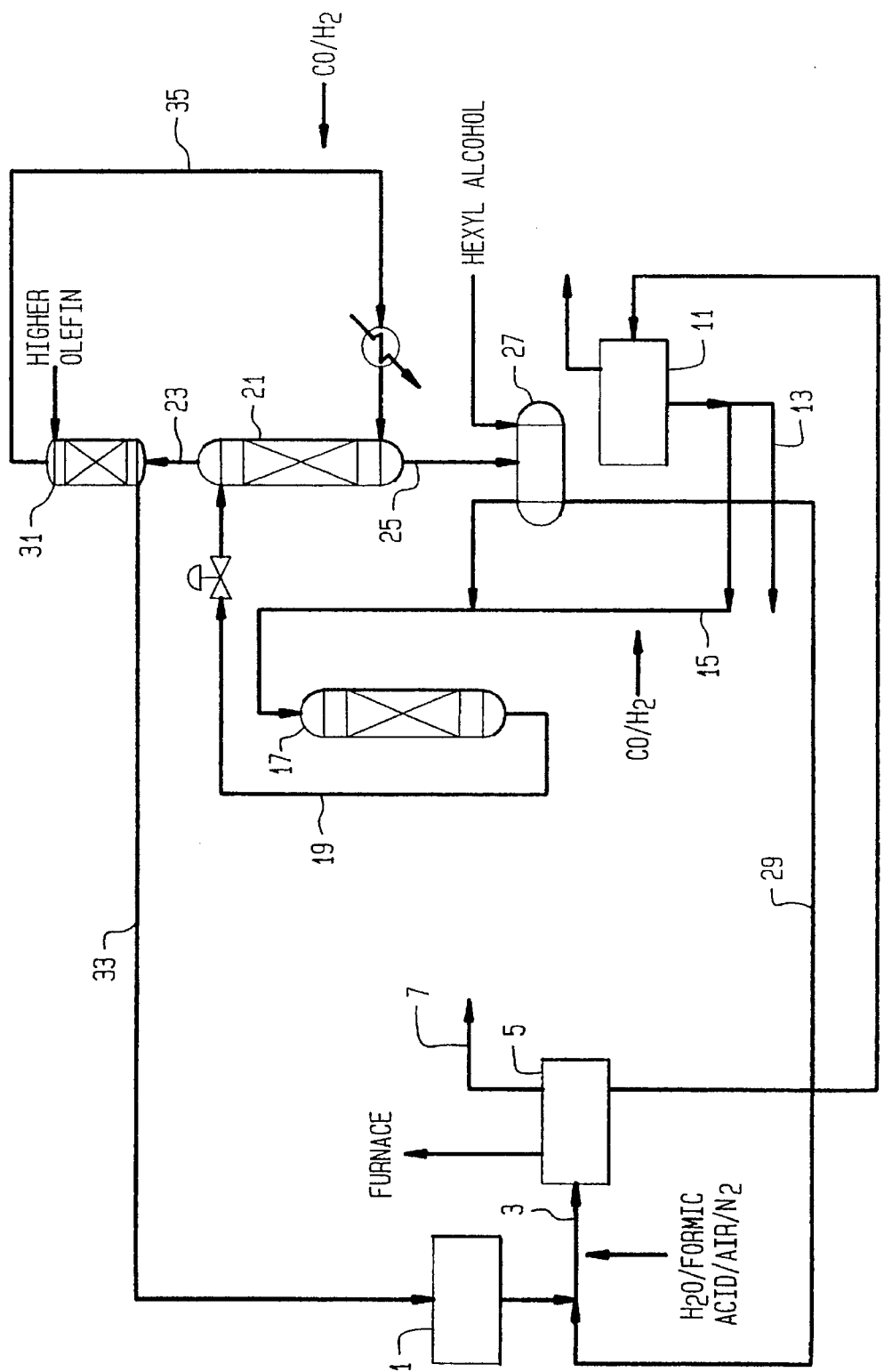
FIG. 1 illustrates an oxo process including a method for removing cobalt values wherein an acid-air cobalt demetalling step is disposed upstream of the stripping step in a Cobalt Flash process.

In the preforming step of the cobalt oxo process in which cobalt salts are convened to hydrido cobalt tetracarbonyl, increased catalytic activity can be observed versus conventional preformer catalyst when the catalytic metal, e.g., palladium, is preferentially disposed about the exterior surface of the catalyst substrate or support, e.g., an activated carbon substrate. Even more preferably, the metal penetrates no more than about 0.1 to 0.15 mm into the surface of an extruded catalyst support or substrate having a diameter of about 2.0 mm or onto the surface of a granular support with average size of about 2.5 to 5 mm. The preforming step is illustrated by the following equations (1) and (2) in which cobalt formate is the illustrative salt undergoing conversion to $HCo(CO)_4$ and palladium is the illustrative preformer catalyst:

$$3Co(COOH)_2 + 3H_2 + 8CO \leftrightarrow Co[Co(CO)_4]_2 + 6HCOOH \quad (1)$$

$$Co[Co(CO)_4]_2 + 2HCOOH \rightarrow 2HCo(CO)_4 + Co(COOH)_2 \quad (2)$$

In equation (2) above, the hydrido cobalt carbonyl (i.e., $HCo(CO)_4$) is liberated from $Co[Co(CO)_4]$ by the formic acid which is present as a by-product of the hydroformylation process and also as a result of the preforming reaction shown in equation (1) above.

The preformer step involves the reaction of cobalt salts such as cobalt formate or cobalt acetate in aqueous solution in the presence of hydrogen and carbon monoxide at elevated pressure of about 3000 to 4000 psig (20.8 to 27.7 MPa) and at a temperature of from about 120° to 150° C. over a shell-type, metal on substrate, catalyst. In the operation of the oxo process the cobalt formate or cobalt acetate in aqueous solution is obtained from an acid/air demetalling step, such as is disclosed in U.S. Pat. No. 5,237,105, issued Aug. 17, 1993, to Summerlin, or from the Cobalt Flash stripper bottom, followed by concentration in an evaporator or flash unit. An organic phase such as an alcohol or mixture of aldehyde/alcohol/hydrocarbon (i.e., crude oxo product) is processed with the aqueous solution to improve the overall conversion. Since hydrido cobalt tetracarbonyl has limited solubility in water but high solubility in organic material, coprocessing with an organic phase prevents the deposition of cobalt on the catalyst's surface because the hydrido cobalt tetracarbonyl is continuously extracted into the organic phase. The extraction of the product carbonyl into the organic phase effectively drives the reaction to higher conversion. The carbon number of the organic phase is typically $C_6$ to $C_{15}$.

Once hydrido cobalt carbonyl is extracted into the organic phase, it can form dicobalt octacarbonyl by the following reversible reaction:

$$2HCo(CO)_4 \leftrightarrow Co_2(CO)_8 + H_2$$

The dicobalt octacarbonyl can also dissociate in the presence of an alcohol as indicated below:

$$3Co_2(CO)_8 \leftrightarrow 2(Co(ROH)_6)^{2+}(Co(CO)_4)_2^- + 8CO$$

Dicobalt octacarbonyl can also disproportionate with water according to the following reaction:

$$3Co_2(CO)_8 \leftrightarrow 2Co^{2+}(Co(CO)_4)_2^- + 8CO$$

The preformer reaction resulting in the formation of cobalt carbonyl compound is promoted with a noble metal catalyst, in particular a catalyst selected from the metals of Group IB and VIII of the Periodic Table. Representative examples of useful catalyst material include gold, platinum and palladium. Palladium is the preferred catalytic metal.

In accordance with the present invention it is highly advantageous to utilize in the preformer reaction a shell-type, metal on substrate, catalyst. Examples of such types of catalyst are disclosed in International Patent Application No. WO 93/18856 (Schick et al.), published on Sep. 30, 1993, and which is incorporated herein by reference. In this particular type of preparation, the preferred shell-type, metal on substrate, catalyst is one which contains 0.3 to 5, in particular 0.5 to 2% by weight palladium on an activated carbon substrate or support, with respect to the dried catalyst. The catalyst is obtained by impregnating the substrate with an aqueous palladium salt solution, by precipitating the palladium and by reduction (activation). In catalyst manufacture, the impregnation step is the most important step in that it is the primary determinant for both metal location and crystallite size. In particular with activated carbon substrates, it has been found that by carefully controlling the pH of the substrate during the metals impregnation step, the metal can be made to deposit preferentially in a thin shell on the exterior surface of the catalyst substrate. In order to produce the preferred shell-type catalyst, an alkaline-reaction activated carbon, having in particular a pH value of at least 8, is impregnated with the palladium salt solution. The pH of the impregnating solution is carefully adjusted to allow precipitation of the metal and the excess fluid is separated after it has reached a pH value of at least 1, in particular at least 3 and preferably at least 4. The separation of the excess fluid is conducted by filtering and washing with water. Subsequent reduction with gaseous hydrogen completes the preparation. A particularly high activity and long service life, as well as a particularly simple and economical product process, are thus obtained. The volume of the aqueous palladium salt solution is about the same as the total pore volume of the activated carbon. The activated carbon is preferably agitated during addition of the aqueous palladium salt solution.

Figure 2:
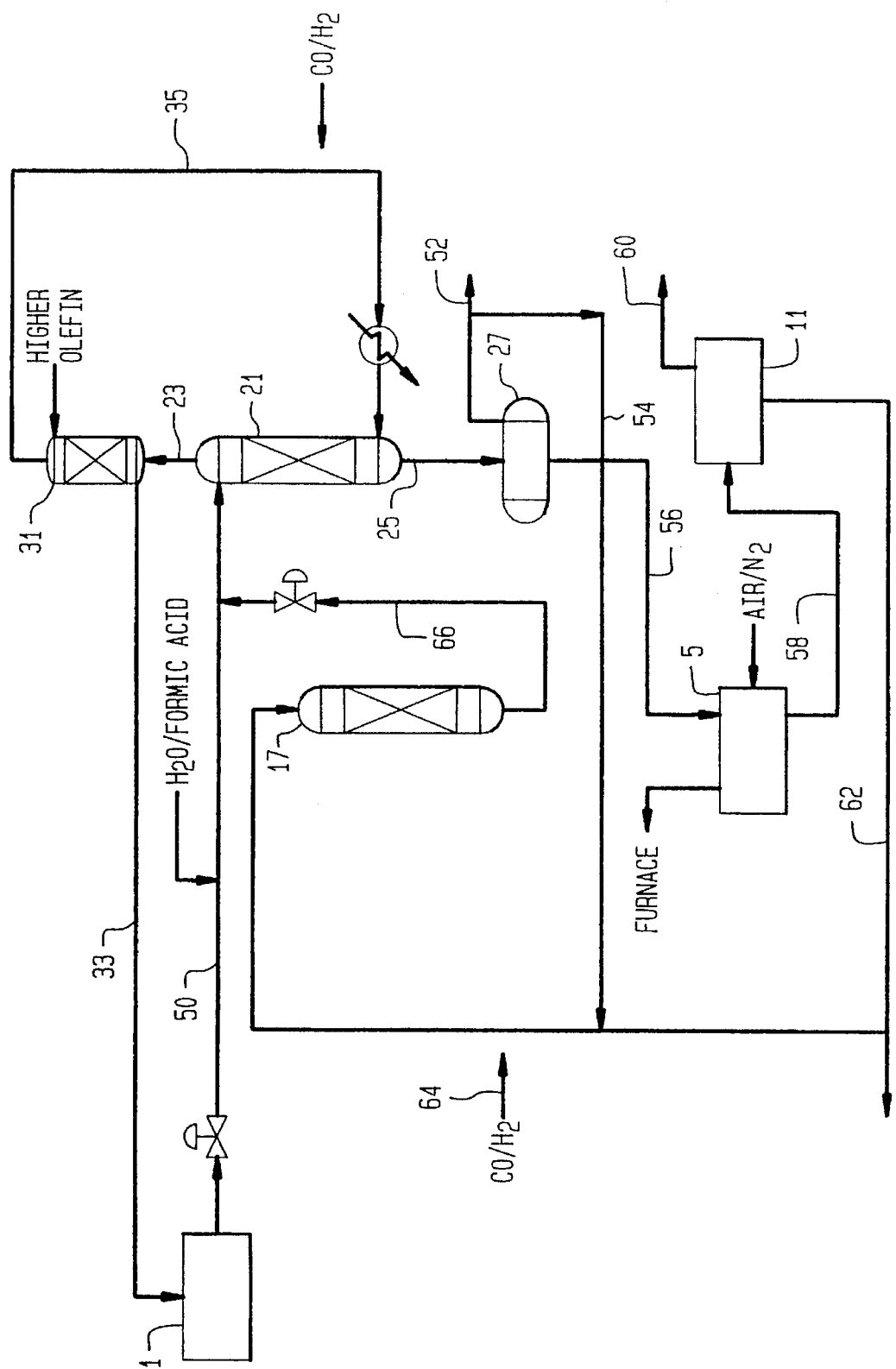
FIG. 2 illustrates an oxo process including a method for removing cobalt values wherein an acid-air cobalt demetalling step is disposed downstream of the stripping step in a Cobalt Flash process.

Catalysts prepared by this method will typically have palladium deposited on the surface of the carbon substrate or support to a depth between 0.10 to 0.15 mm. In contrast, a wet impregnation without the specified pH control will result in metal being dispersed more uniformly from the center of the substrate outwardly. This shell-type catalyst can be preferentially used to preform cobalt salts in aqueous solutions to hydrido cobalt carbonyl. FIGS. 1 and 2 depict process schemes utilizing the preforming step.

FIG. 1 generally depicts a method for removing cobalt values from the crude product of a cobalt-catalyzed hydroformylation reaction formed from an olefinic feedstock having a carbon number in the range of $C_4$ to $C_{14}$, preferably $C_5$ to $C_7$. The crude product typically contains cobalt compounds in addition to an organic hydroformylation reaction product.

An olefinic feedstock and syn gas are introduced into oxo reactor 1, wherein hydroformylation is conducted under conventional conditions to yield a crude hydroformylation product containing aldehydes, alcohols, by-products and cobalt catalyst compounds. This crude product is carried via conduit 3 where it is contacted with a stream of oxygen-containing gas, an organic acid and water, thereby producing a substantially cobalt-free organic hydroformylation reaction product and a water soluble cobaltous salt aqueous product, to settling drum or demetalling drum 5. In demetalling drum 5 the substantially cobalt-free crude product is separated from the water soluble cobaltous salt aqueous product. The substantially cobalt-free organic hydroformylation reaction product is diverted overhead via conduit 7 for further downstream treatment such as distillation and/or hydrogenation. The water soluble cobaltous salt aqueous product is carried via conduit 9 to evaporator 11 which concentrates the water soluble cobaltous salt, thereby producing a concentrated aqueous solution of cobaltous salt and a substantially cobalt-free water containing the organic acid, whereby the concentrated aqueous solution of cobaltous salt is separated from the substantially cobalt-free water containing the organic acid. The substantially cobalt-free water containing the organic acid is recycled via conduit 13 to oxo reactor 1. Whereas the concentrated aqueous solution of cobaltous salt is contacted with an alcohol stream and synthesis gas within conduit 15 before this mixture is passed to preformer reactor 17. In preformer reactor 17 the concentrated aqueous solution of cobaltous salt is converted to a cobalt carbonyl under catalytic conditions. The cobalt carbonyl from preformer 17 is carried via conduit 19 to stripper reactor 21 where it is contacted with a stream of stripping gas at a temperature of not greater than 100° C. and at a pressure below 10.13 bar, the pressure of the cobalt compounds at the contacting temperature, to entrain volatile cobalt compounds in the stripping gas and to generate as bottoms alcohol products and dissolved cobaltous salts; whereby the entrained volatile cobalt compounds are taken out overhead via conduit 23 and the alcohol products and dissolved cobaltous salts are taken out as bottoms via conduit 25. The alcohol products are separated from the dissolved cobaltous salts in settling drum 27. The dissolved cobaltous salts are typically in an aqueous phase, e.g., an aqueous salt product, which can be readily separated from the organic phase, i.e., the alcohol products, by gravity settling. The alcohol products from settling drum 27 are preferably recycled to conduit 15 for mixing with the cobaltous salt upstream of preformer reactor 17 to act as a preformer solvent. The cobaltous salt from settling drum 27 is preferably recycled via conduit 29 to conduit 3 for further demetalling. Finally, the volatile cobalt compounds from conduit 23 are introduced into absorber 31 where they are contacted with olefinic feedstock, whereby the volatile cobalt compounds are absorbed into the olefinic feedstock and recycled to oxo reactor 1 via conduit 33. Reflux from absorber 31 is returned to stripper reactor 21 via reflux conduit 35. Optionally, syn gas may also be fed into stripper reactor 21 via reflux conduit 35.

In FIG. 2 an olefinic feedstock and syn gas are introduced into an oxo reactor 1, wherein hydroformylation is conducted under conventional conditions to yield a crude hydroformylation product containing aldehydes, alcohols, byproducts and cobalt catalyst compounds. This crude product is carried via conduit 50 where it is contacted with water and an organic acid, such as formic acid. The treated crude product is thereafter contacted with a stream of stripping gas in stripper reactor 21. The stripping typically occurs at a temperature of not greater than 100° C. and at a pressure below 10.13 bar, the pressure being lower than the decomposition pressure of the cobalt compounds at the contacting temperature, to entrain volatile cobalt compounds in the stripping gas, whereby the entrained volatile cobalt compounds are taken out overhead via conduit 23 and organic hydroformylation reaction products containing water soluble cobaltous salts dissolved therein are taken out as bottoms via conduit 25. The water soluble cobaltous salt is then separated from the organic hydroformylation reaction products by means of settling drum 27. The organic hydroformylation reaction product may be diverted from conduit 52 via conduit 54 and recycled to the preformer reactor 17. The water soluble cobaltous salt is carried via conduit 56 to settling drum or demetalling drum 5 where it is contacted with a stream of oxygen-containing gas, an organic acid and water thereby producing a water soluble cobaltous salt aqueous product. The oxygen should be present in an amount such that the organic acid only sees the water. Thereafter, the water soluble cobaltous salt aqueous product is carried via conduit 58 to evaporator 11 which forms a concentrated aqueous solution of cobaltous salt and a substantially cobalt-free water containing the organic acid. The concentrated aqueous solution of cobaltous salt is then separated from the substantially cobalt-free water containing the organic acid, whereby the substantially cobalt-free water containing the organic acid is recycled via conduit 60 to stripper reactor 21, diverted to the optional water wash treatment step, or diverted to hydrogenation. The concentrated aqueous solution of cobaltous salt is carried via conduit 62 either to preformer reactor 17 or recycled to oxo reactor 1. However, prior to being fed to preformer reactor 17, the concentrated cobaltous salt is contacted with an alcohol stream, a cobalt-free organic hydroformylation reaction product, or a hydrogenation product delivered via conduit 54 and syn gas which is delivered via conduit 64. This mixture is then passed to preformer reactor 17 where the concentrated aqueous solution of cobaltous salt is converted to a cobalt carbonyl. The cobalt carbonyl is then carried via conduit 66 and 50 to stripper reactor 21. Finally, the volatile cobalt compounds which are carried from stripper reactor 21 via conduit 23 are sent to absorber 31 wherein they are returned to oxo reactor 1 via conduit 33.

EXAMPLE 1

To establish a reference case, a 1% by weight palladium on 2.5–5.0 mm granular carbon catalyst (catalyst 1) with metal evenly distributed throughout the carbon support was tested for preforming activity in a fixed bed tubular reactor. Test conditions for this example 1 were as follows: 5.0 LHSV, 1:1 cobalt water (0.94 wt. % cobalt) to hexyl alcohol, 3000 psig (20.8 MPa), 1:1 $H_2/CO$ molar ratio, and 120° C. LHSV equals the total volumetric liquid rate (i.e., cc/hour) divided by catalyst volume (i.e., cc). Catalyst 1 is representative of the conventional palladium/carbon preforming catalyst technology, in which the palladium is uniformly distributed through the catalyst particle.

TABLE 1

| Catalyst | % Cobalt Formate Conversion | 1st Order Reversible[a] Rate Constant, 1/hour |
| --- | --- | --- |
| 1 | 20.0 | 1.14 |
| 2 | 39.5 | 2.68 |

[a]1st order reversible rate constant (k) is equal to (LHSV) * $X_{ae}$ * $(-\ln(1 - X_a/K_{Ae}))$, wherein $X_{ae}$ is the fraction of cobalt formate converted at equilibrium and $X_A$ is the fraction of cobalt formate converted at time t = 1/LHSV.

As indicated in Table 1, the extent of preforming activity on catalyst 1 is quantified at 20% conversion of cobalt formate to hydrido cobalt tetracarbonyl. Considering test conditions and catalyst volume, the 20% conversion corresponds to a first order reversible kinetic rate constant of 1.14 1/hr.

EXAMPLE 2

A shell-type, metal on substrate, catalyst according to the present invention was prepared from a 1% palladium on a 2.5–5.0 mm granular carbon substrate, with the metal preferentially loaded on the exterior surface of the carbon substrate. Test conditions for this example 2 were the same as those used in example 1 above. The results from this example 2 are set forth above in Table 1.

Improved performance was observed for catalyst 2, relative to catalyst 1, as indicated by a two-fold increase in cobalt formate conversion. The 39.5% conversion corresponds to a first order reversible kinetic rate constant of 2.68 1/hr.

While I have shown and described several embodiments in accordance with my invention, it is to be clearly understood that the same are susceptible to numerous changes apparent to one skilled in the art. Therefore, I do not wish to be limited to the details shown and described but intend to show all changes and modifications which come within the scope of the appended claims.

What is claimed is:

1. A process for preparing oxo alcohols and aldehydes by the cobalt catalyzed hydroformylation of $C_2$ to $C_{17}$ linear or branched monoolefins with subsequent hydrogenation of the hydroformylation product, in which oxo process aqueous solutions of cobalt salts are convened to active hydrido cobalt carbonyl species in a preformer reactor under preforming reaction conditions, the improvement characterized by said preformer reactor containing a shell-type, metal on substrate, preformer catalyst.

2. The process according to claim 1 wherein said oxo process aqueous solutions of cobalt salts are converted to active hydrido cobalt carbonyl species in a preformer reactor in the presence of hydrogen and carbon monoxide at a pressure in the range between about 20.8 to 27.7 MPa and a temperature in the range between about 120° to 150° C.

3. The process according to claim 1 wherein said shell-type, metal on substrate, preformer catalyst comprises 0.3 to 5% by weight metal on said substrate.

4. The process according to claim 3 wherein said shell-type, metal on substrate, preformer catalyst is formed by the following steps:

impregnating said substrate with an aqueous metal salt solution;

precipitating said metal; and reducing said metal.

5. The process according to claim 4 wherein said aqueous metal salt solution is an aqueous salt solution of a metal selected from the group consisting of: Group IB and Group VIII of the Periodic Table.

6. The process according to claim 5 wherein said metal is palladium.

7. The process according to claim 4 wherein said substrate is one selected from the group consisting of: activated carbon, ion exchange resins, silica, alumina and zeolites.

8. The process according to claim 7 wherein said substrate is an alkaline-reaction activated carbon having a pH value of at least 8.

9. The process according to claim 8 further comprising the step of separating any excess aqueous salt solution subsequent to said impregnation step after said aqueous salt solution has reached a pH value of at least 1.

10. The process according to claim 4 wherein said metal contained within said aqueous metal salt solution impregnates the surface of said substrate to a depth between about 0.10 to 0.15 mm.

11. The process according to claim 1 wherein said substrate is an extruded substrate.

12. The process according to claim 11 wherein said substrate is a granular substrate having a diameter of between about 2.5 to 5 mm.

* * * * *